United States Patent [19]

Stadler et al.

[11] 4,380,625

[45] Apr. 19, 1983

[54] PROCESS FOR THE PREPARATION OF PURIFIED AMINOGLYCOSIDE ANTIBIOTICS

[75] Inventors: Peter Stadler, Hann; Wolfgang Koebernick, Wuppertal; Samir Samaan, Wuppertal; Wolfgang Gau, Wuppertal, all of Fed. Rep. of Germany

[73] Assignee: Bayer Aktiengesellschaft, Leverkusen, Fed. Rep. of Germany

[21] Appl. No.: 220,640

[22] Filed: Dec. 29, 1980

[30] Foreign Application Priority Data

Jan. 11, 1980 [DE] Fed. Rep. of Germany ....... 3000841

[51] Int. Cl.$^3$ ............................................. C07H 15/22
[52] U.S. Cl. .................................. 536/13.9; 536/13.6; 536/16.8; 536/16.9
[58] Field of Search .................... 536/17 R, 13.9, 16.8

[56] References Cited

U.S. PATENT DOCUMENTS

| | | | |
|---|---|---|---|
| 4,107,435 | 8/1978 | Ross | 536/17 R |
| 4,180,565 | 12/1979 | Mallams et al. | 536/17 R |
| 4,190,722 | 2/1980 | Voss et al. | 536/17 R |
| 4,224,315 | 9/1980 | Stadler et al. | 536/17 R |

*Primary Examiner*—Johnnie R. Brown
*Attorney, Agent, or Firm*—Sprung, Horn, Kramer & Woods

[57] ABSTRACT

The invention relates to an improved process for the isolation and purification of aminoglycoside antibiotics of Formula (I) as defined herein combining selective lipophilization of the compound of Formula (I) in the crude product obtained by fermentation with controlled liquid/liquid extraction.

16 Claims, No Drawings

PROCESS FOR THE PREPARATION OF PURIFIED AMINOGLYCOSIDE ANTIBIOTICS

The invention relates to an unobvious improved process for the isolation and purification of aminoglycoside antibiotics of the formula

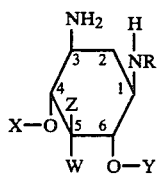

wherein
X denotes a radical of the formula

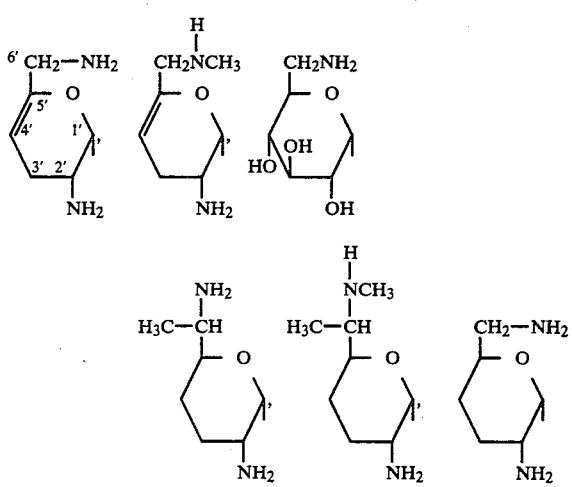

Y denotes a radical of the formula

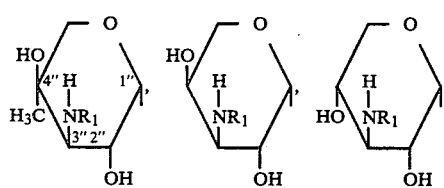

R denotes a hydrogen atom or an ethyl group,
$R_1$ denotes a $C_1$ to $C_6$ alkyl group, preferably a methyl or ethyl group, and
one of the radicals Z or W denotes a hydrogen atom and the other radical Z or W denotes a hydrogen atom or a hydroxyl group.

The process according to the invention is preferably used for the purification or preparation of sisomicin, 5-episisomicin, netilmicin, gentamicin and 3''-N-demethyl-3''-N-ethylsisomicin.

The compounds of the formula (I) are known aminoglycoside antibiotics. Some of them are obtained biosynthetically by culturing, in an aqueous nutrient medium under specific conditions, a strain which produces the antibiotic in question, or by chemical modification of an antibiotic obtained by the abovementioned biosynthetic process.

The present invention, as defined herein, relates to a multi-stage working-up process which utilises a new, advantageous concept of isolating and purifying aminoglycosides; it combines selective lipophilisation of the particular compound of the formula (I) in the crude product obtained by fermentation with controlled liquid/liquid extraction of this lipophilised product.

The lipophilisation is achieved by providing the amino groups contained in the compounds of the formula (I) with suitable protective groups. After the desired aminoglycoside derivative has been separated off in a pure form by liquid/liquid extraction, the protective groups are split off again and the desired aminoglycoside of the formula (I) is obtained in a pure form.

In the case of the biosynthetic compounds, the fermentation broth is pre-purified and the amino groups of the desired compound and of the undesired concomitant substances are reacted with protective group reagents selected for the individual case.

In the case of synthetically modified compounds, the pre-purified fermentation broth of a biosynthetically produced aminoglycoside is likewise used as the starting material, the subsequent step being a selective reaction with protective group reagents selected for the individual case. The desired chemical reaction, for example the introduction of an ethyl group into the 1-position or the replacement of the methyl group in the 3''-position by an ethyl group, is carried out using the selectively blocked intermediate products thus obtained, this being followed, if appropriate, by a further reaction with protective group reagents.

According to the present invention there is provided a process for the preparation of a pure aminoglycoside antibiotic, in which (a) a pre-purified compound of formula (I), as defined previously, is acylated or arylsulphenylated to give a compound of the formula

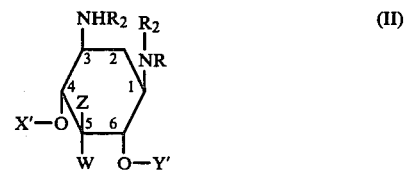

wherein X' represents a radical of the formulae

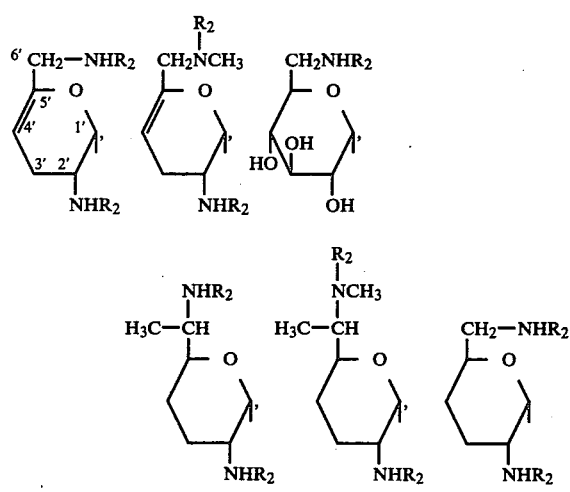

Y' represents a radical of the formulae

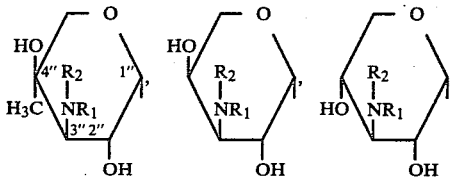

the radicals $R_2$ are identical or different and represent a hydrogen atom or an acyl or arylsulphenyl protective group, with the proviso that at most two of the radicals $R_2$ represent hydrogen atoms, and R, $R_1$, Z and W have the abovementioned meaning, and optionally, where at least one of the radicals $R_2$ denotes a hydrogen atom, a chemical derivative is formed on one or more of the unprotected amino groups, (b) the compound of formula (II) from step (a) is subjected to liquid/liquid extraction in a two-phase aqueous/organic solvent system and is isolated from the extracts, and optionally, where at least one of the radicals $R_2$ denotes a hydrogen atom, a chemical derivative is formed on one or more of the unprotected amino groups, and (c) the protective group(s) are split off.

The term "pure" used herein means that the aminoglycoside antibiotic is of sufficient purity for direct pharmaceutic use and, includes the isolation, if desired, of component of aminoglycoside antibiotic mixtures, whereas "pre-purified" merely refers to the removal of the major contaminants from the prior preparative process.

The particular acyl or arylsulphenyl protective group suitable for the individual case and the liquid/liquid extraction system can easily be established by preliminary experiments, with the assistance of suitable analytical methods, preferably by Craig distribution or high pressure liquid chromatography (HPLC).

In contrast, the isolation and purification processes hitherto used comprise many stages, are troublesome and are associated with high losses in yield. For example, sisomicin (antibiotic 66-40) is purified in the following manner, as described in DE-OS (German Published Specification) No. 1,932,309, Examples 2 to 5:

The fermentation broth is acidified, the mycelium is filtered off and the filtrate is neutralised with aqueous ammonia and, after removal of the calcium ions, treated with a cation exchanger resin, whereby the desired aminoglycoside is bonded, in addition to a considerable proportion of other organic and inorganic compounds. The resin is washed with water and subsequent elution with aqueous ammonia gives sisomicin as a 50% strength crude product. This product is further purified by ion exchanger chromatography and converted into the sulphate by treatment with sulphuric acid, and this sulphate is further purified by column chromatography and recrystallisation and finally converted back into the free base. The yield is less than 10%, relative to the 50% strength crude product.

The preparation of the aminoglycoside antibiotics provided with aryl or arylsulphenyl protective groups (stage (a) of the process according to the invention) is known, for example from European Published Patent Application 57.

It is expedient to carry out pre-purification of the fermentation broths by a procedure in which they are treated, in a manner which is in itself known, with a cation exchanger resin, onto which the aminoglycoside antibiotic in question is bonded, the resin is washed with water and the aminoglycoside is then eluted with aqueous ammonia and the ammonia removed.

Suitable aryl or arylsulphenyl protective groups are known, for example from Houben-Weyl, Methoden der organischen Chemie (Methods of Organic Chemistry), Volume XV, Georg Thieme Verlag, Stuttgart, 1974. Preferred examples of such protective groups are acyl groups of the general formula

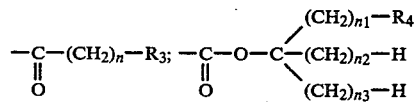

wherein $R_3$ and $R_4$ independently denote a hydrogen atom or an optionally substituted phenyl radical and n, $n_1$, $n_2$ and $n_3$ independently of one another denote 0, 1, 2, 3, 4 or 5, and sulphenyl protective groups of the general formula $$-S-R_5$$

wherein $R_5$ denotes an optionally substituted phenyl or di- or tri-phenylmethyl radical.

An optionally substituted phenyl radical, $R_3$, $R_4$ or $R_5$ preferably denotes a phenyl radical which is optionally monosubstituted or disubstituted by nitro, $C_1$-$C_4$-alkoxy, halogen or phenyl.

In order to prepare these selectively N-protected amino-trisaacharides, the unprotected pre-purified compound of formula (I) is reacted in stage (a) with, for example, a compound of the following formula

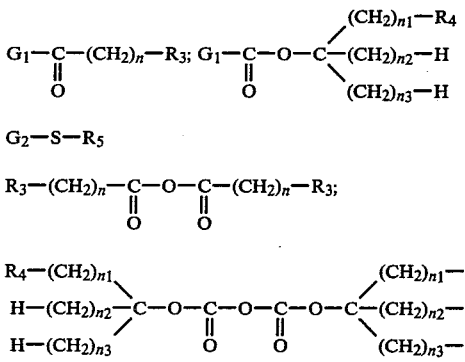

wherein $G_1$ denotes a halogen atom or another acylation reaction-leaving group, preferably a group which activates an ester, $G_2$ denotes a halogen atom or another sulphenylation reaction-leaving group, preferably a group which activates an ester, and $R_3$, $R_4$, $R_5$, n, $n_1$, $n_2$ and $n_3$ have the abovementioned meaning.

The introduction of the protective groups is generally carried out, starting from the crude products obtained by fermentation, in an inert solvent at a temperature from $-30°$ C. and $+50°$ C., preferbly between $0°$ C. and $25°$ C., and if appropriate in the presence of a base. The reaction product is then worked up in the customary manner.

Radical G₂ is preferably a chlorine atom or a p-nitrophenoxy radical. Examples of sulphenylating reagents which may be mentioned are tritylsulphenyl chloride, o-nitrophenylsulphenyl chloride, 2,4-dinitrophenylsulphenyl chloride, 2,4,5-trichlorophenylsulphenyl chloride, pentachlorophenylsulphenyl chloride, o-nitrophenylsulphenic acid p-nitrophenyl ester, 2,4-dinitrophenylsulphenic acid p-nitrophenyl ester, 2,4,5-trichlorophenylsulphenic acid p-nitrophenyl ester and pentachlorophenylsulphenic acid p-nitrophenyl ester.

These reactive sulphenic acid derivatives are either already known (see example Houben-Weyl, Methoden der organischen Chemie (Methods of Organic Chemistry), Volume XV, 1, pages 203 to 222, Georg Thieme Verlag, Stuttgart, 1974), or can be prepared by processes analogous to those for the compounds which are already known.

Examples of acylating reagents which may be mentioned are acetic anhydride, acetyl chloride and diethyl pyrocarbonate, the use of dialkylpyrocarbonates as protective group reagents in general being particularly preferred for the preparation of N-alkyl-oxycarbonyl derivatives.

ossible diluents for the reaction with sulphenic acid halides are either inert organic solvents, such as chloroform and toluene, or, preferably, water-miscible solvents, such as dioxane, dimethylformamide and dimethoxyethane, and mixtures thereof with water.

The reactions with activated esters of the above-mentioned sulphenic acids are preferably carried out in inert organic solvents, such as chloroform, dimethylformamide or pyridine, or mixtures of such solvents with alcohols, preferably methanol or ethanol. The acyl compounds according to the invention are prepared in any desired inert organic solvents, in water or in mixtures of organic solvents and water, mixtures of methanol, ethanol or acetone and water being preferred.

All the basic compounds customary in organic chemistry, such as triethylamine, pyridine and diazabicyclononene, can be employed as the bases; however, alkali metal hydroxides or carbonates, such as sodium hydroxide solution or sodium carbonate, are preferably used.

The sulphenylation or acylation reactions can be carried out either under normal pressure or under increased pressure. In general, the reactions are carried out under normal pressure.

Some variants of stage (a) of the process according to the invention, for various aminoglycosides, are described below by way of example. In the case of sisomicin, for example, a procedure can be followed in which acetic anhydride is added dropwise, at 5° C., to an aqueous crude sisomicin solution containing about 10% of sisomicin base. The sisomicin present in the solution and also the remaining amino compounds are thereby acylated on the primary amino groups. A mixture which contains 1,3,2',6'-tetra-N-acetylsisomicin is obtained in this manner. A crude gentamicin product reacts under the same conditions to give a mixture which contains 1,3,2',6'-tetra-N-acetylgentamicin C 1a. If pyrocarbonic acid dimethyl ester or diethyl ester is used as the protective group reagent and crude sisomicin is used as the substrate, 1,3,2',6'-tetra-N-methoxycarbonylsisomicin or -ethoxycarbonylsisomicin is formed in aqueous alcohol at low reaction temperatures. Other compounds which are present in the crude product employed and carry NH₂ groups likewise react, at the amino groups, with the pyrocarbonic acid esters, the corresponding urethanes being formed. The reaction of crude sisomicin with o-nitrophenylsulphenic acid p-nitrophenyl ester in a mixture of methanol and methylene chloride as the solvent leads to 1,3,2',6'-tetra-N-(o-nitrophenylsulphenyl)-sisomicin. All the remaining substances which have primary amino groups and are contained in the crude product likewise react with the protective group reagent. Even in the case of crude products obtained by fermentation, the abovementioned reactions proceed smoothly and with a high selectivity to give partially blocked derivatives in which the primary amino groups are in each case protected but the secondary amino groups still carry a reactive hydrogen atom.

If desired, it is also possible to provide all the amino groups, that is to say the primary and secondary amino groups with protective groups; the protective group reagents mentioned previously again being preferably used. This reaction is carried out in an inert solvent or in solvent mixtures, if appropriate with the addition of water, at temperatures between 0° and 100° C., preferably between 25° and 70° C., and if appropriate in the presence of a base. Since the secondary amino groups are in general less reactive than the primary amino groups, it is expedient to use an excess of protective group reagent; the water content of the solvent mixture used is kept as low as possible and, if necessary, the reacton is carried out at elevated temperature. Possible solvents for the reactions in question are, in principle, any solvents which dissolve the starting materials and either do not themselves react with the protective group reagents in question, or react with the protective group reagents in question with more difficulty than with the amino groups to be reacted. Examples which may be mentioned are chloroform, methylene chloride, ethanol, methanol, acetone and dioxane. Possible auxiliary bases are the compounds already mentioned. If, for example, the 1,3,2',6'-tetra-N-acetylsisomicin already mentioned is reacted with isopropylchloroformate at about 60° C. in ethanol/water (9:1) in the presence of sodium carbonate, 1,3,2',6'-tetra-N-acetyl-3''-N-isopropoxycarbonylsisomicin is obtained. The preparation of the per-N-protected amino-trisaccharides can also be effected in one stage. Thus, for example, sisomicin reacts completely with excess dimethyl pyrocarbonate in methanol to give penta-N-methoxycarbonylsisomicin.

However, in many cases it is expedient to provide penta-N-protected compounds with different protective groups. By suitable choice of the protective groups, the lipophilic or hydrophilic character of the compounds of the formula (II) can be steered in a controlled manner such that an optimum ease of separation of undesired by-products by liquid/liquid extraction is achieved.

The extraction systems used according to the invention are aqueous-organic solvent systems. In general, a procedure is followed in which, after the extraction, the desired amino-trisaccharide derivative is in the organic phase. Besides water, a suitable aqueous phase is, above all, aqueous ammonium hydroxide, for example a saturated solution of ammonia in water or solutions with a lower percentage content of ammonium hydroxide. Instead of ammonium hydroxide, it is also possible to add other basic auxiliaries, such as organic amines, for example methylamine, dimethylamine and trimethylamine, to the aqueous phase. However, inorganic compounds, such as alkali metal hydroxides, can also be used as basic auxiliaries.

Suitable organic phases are solvents which are water-immiscible or only slightly water-miscible and are inert towards the product mixtures employed in the extraction, for example hydrocarbons (such as toluene, xylene, ethylbenzene and hexane), chlorinated hydrocarbons, (such as methylene chloride, 1,2-dichloroethane and 1,2-dichloropropane), esters (such as ethyl acetate, ethyl propionate and tributyl phosphate), ethers (such as diethyl ether), or alcohols (such as n-butanol, propan-2-ol and n-pentanol). Further organic phases which are to be particularly preferred are mixtures of water-immiscible solvents and other organic solvents, for example methylene chloride/propan-2-ol, methylene chloride/n-hexane, methylene chloride/n-butanol, 1,2-dichloroethane/n-hexane, butanol/n-hexane, methylene chloride/propan-2-ol/n-hexane and ethyl acetate/n-hexane. In general, it is advantageous for the organic phases which are used in the context of the extraction process to be saturated with ammonium hydroxide.

It can also be particularly advantageous to use, for the extraction, those two-phase systems which are formed when aqueous ammonium hydroxide solutions are brought together with an organic solvent (A) which is immiscible with aqueous ammonium hydroxide or miscible with aqueous ammonium hydroxide only to a limited extent and with a free organic solvent (B), solvent (B) optionally being miscible with aqueous ammonium hydroxide the components are then mixed thoroughly until equilibrium is established and the phases are then allowed to separate from each other and used for the extraction; examples being two-phase systems which are obtained from mixtures of n-butanol, ammonium hydroxide and n-hexane or methylene chloride, ammonium hydroxide and propan-2-ol.

The ratio of organic phase to aqueous phase can be varied within wide limits. This ratio is preferably 0.5:1 to 30:1, and very particularly preferably 5:1 to 20:1. The content of the desired amino-trisaccharide compound in the extract can be varied within wide limits by varying the amount of the extraction agent and the number of the extraction stages. The extraction agent employed is in general so chosen that extracts which contain the desired amino-trisaccharide derivative in a concentration of 0.1 to 15% are obtained.

The amount of solvent in the aqueous crude solutions employed for the extraction is so chosen that a content of amino-trisaccharide derivative of between 1 and 20% results, 2 to 10% strength solutions preferably being employed. In this case, the percentage data are percentages by weight.

The number of extraction stages necessary for optimum extraction is established in a known manner by preliminary experiments, for example via a distribution curve.

The temperature of the extraction can be varied within wide limits. In general, the extraction is carried out at a temperature between 10° and 60° C. It can be carried out under normal pressure, reduced pressure or increased pressure. Possible extraction units are the known extraction systems, for example mixer/separators, centrifugal extractors or column systems, such as spray columns, stirred columns, such as Scheibel columns, or pulsating columns, such as pulsating perforated tray columns. In particularly simple cases, extractions can also be carried out by mixing and allowing to settle in one reaction vessel, for example in a stirred kettle. On a laboratory scale, it is also possible to use separating funnels, in the known manner, for carrying out the extraction. If columns are used, the extraction is preferably carried out as a countercurrent extraction.

In order to isolate the desired product, the extraction phase which contains the desired amino-trisaccharide derivative, that is to say in general the organic phase, is concentrated or completely evaporated, in which case, in order to protect the product, those evaporator units in which the residence time of the product is as short as possible, for example, falling film evaporators or thin layer evaporators, are preferably chosen. Evaporation of the solvent is preferably carried out under reduced pressure.

Using the process according to the invention, not only can aminoglycoside antibiotics be separated off from their impurities, but also it is possible to separate aminoglycoside mixtures, such as are formed by culturing the corresponding micro-organisms, into their components.

Gentamicin consists of 3 closely related components of the formula

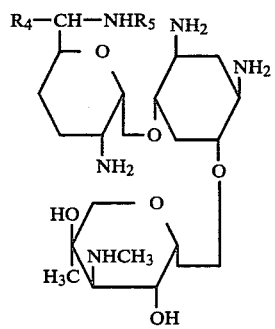

Gentamicin $C_1$    $R_4 = R_5 = CH_3$
Gentamicin $C_2$    $R_4 = CH_3; R_5 = H$
Gentamicin $C_{1a}$    $R_4 = R_5 = H$ Gentamicin contains about 33% of $C_1$, 41% of $C_2$ and 25% of $C_{1a}$. For the separation, gentamicin is treated with acetic anhydride in water, whilst cooling, all the primary amino groups being acylated. After working up, the secondary amino groups are then converted into the corresponding urethane groupings with n-butyl chloroformate in aqueous ethanol. A mixture of compounds is thus obtained which, on a laboratory scale, can be separated by stepwise liquid/liquid extraction in a separating funnel. Concentrated, aqueous ammonium hydroxide is used as the aqueous phase, and the lower phase of the two-phase system which is formed when 7 parts by volume of methylene chloride, 0.4 part by volume of propan-2-ol and 1 part by volume of concentrated ammonium hydroxide are mixed is used as the organic phase. The gentamicin $C_1$ derivative passes into the organic phase and the other two gentamicin derivatives remain in the aqueous phase. If appropriate, the organic phase can also be washed, in countercurrent, with aqueous ammonia.

Where the compound of formula (I) is sisomicin, 5-episisomicin, netilmicin, gentamicin or 3''-N-demethyl-3''-N-ethylsisomicin, the preparation of the present invention may suitably be carried out without the formation of chemical derivatives on any unprotected amino groups.

In the process according to the invention, in the case where at least one of the radicals $R_2$ in the compounds of the general formula (II) represents hydrogen, chemical derivatives can be formed on the unprotected amino group(s) before and/or after the extraction stage. Possible reactions in this context are, inter alia, acylation reactions or reductive acylation of the amino group with aldehydes, such as are described, for example, in DE-OSen (German Published Specifications) Nos. 2,712,160, 2,753,769, 2,832,268, 2,921,973, 2,924,659 and 2,726,712.

A particularly interesting process variant consists in converting a crude amino-trisaccharide of the formula (I), e.g. sisomicin, which has been obtained by fermentation into the corresponding 1,3,2',6'-tetra-N-acyl or -sulphenyl derivative, preferably acetyl derivative, of the formula (II), alkylating, preferably ethylating, the 3"-methylamino group, if appropriate isolating this derivative in a pure form, preferably by counter-current extraction, subsequently demethylating the resulting tertiary 3"-amino group, thereafter, if appropriate, providing the 3"-alkylamino group with a protective group and subjecting the product to the extraction according to the invention.

The procedure according to the invention is to be described below, using the preparation of 1,3,2',6'-tetra-N-acetyl-3"-N-demethyl-3"-N-ethyl-3"-N-isopropoxycarbonylsisomicin as an example.

Crude sisomicin which has been obtained in the customary manner by fermentation, treatment with a cation exchanger and elution of the resin with aqueous ammonia is reacted, as described above, with acetic anhydride in water to give 1,3,2',6'-tetra-N-acetylsisomicin. Reductive alkylation of the 3"-methylamino group with acetaldehyde and sodium boronate to give the 3"-N-ethyl derivative is then carried out.

This tertiary amine is not subjected to oxidative demethylation with an oxidising agent, for example potassium hexacyanoferrate-III in aqueous methanol, in the presence of a base, for example sodium hydroxide, the secondary 3"-ethylamino compound being formed. The subsequent reaction with isopropyl chloroformate in aqueous alcohol (at about 60° C.) in the presence of sodium carbonate, as a base, then gives a crude penta-N-acyl product, which, for purification according to the invention, is subjected to liquid/liquid extraction.

In another embodiment of the process, the tertiary amine obtained as described above can be purified by continuous countercurrent extraction. The pure 1,2',3,6'-tetra-N-acetyl-3"-N-ethyl-sisomicin then obtained can thereafter be subjected to oxidative dealkylation as described.

One of the preferred processes for the preparation of the crude 3"-N-alkylated derivatives of the 4,6-di-O-(aminoglycosyl)-1,3-diaminocyclitols of the formula (II) which contain amino-protective groups in all the positions except for position 3" consists in reacting the corresponding tetra-N-protected compounds, or acid addition salts thereof, with an aldehyde in the presence of a hydrogen donor reducing agent and working up the batch in a manner which is in itself known.

This process, in which the 3"-amino group in a 4,6-di-O-(aminoglycosyl)-1,3-diaminocyclitol reacts with an aldehyde and is simultaneously reduced in situ, is usually carried out at room temperature in the presence of air, although it can be more favourable to carry out the reaction under an inert gas (argon or nitrogen). The reaction usually goes to completion very rapidly, frequently in less than 60 minutes, which can be established by determinations by thin layer chromatography.

Hydrogen donor reducing agents which are used in this process include dialkylaminoborane (for example dimethylaminoborane, diethylaminoborane and, preferably, morpholinoborane), tetraalkylammonium cyanoborohydrides (for example tetrabutylammonium cyanoborohydride), alkali metal borohydrides (for example sodium borohydride) and alkali metal cyanoborohydrides (for example lithium cyanoborohydride and sodium cyanoborohydride).

The process is usually carried out in an inert solvent. The solvent can be an organic or inorganic solvent, in which the selectively protected 4,6-di-O-(aminoglycosyl)-1,3-diaminocyclitol and the other reagents are soluble and which as far as possible reduces or prevents side reactions under the reaction conditions. Although anhydrous aprotic solvents can advantageously be used (for example tetrahydrofuran if the reducing agent is morpholinoborane), a protic solvent is nevertheless usually employed. Suitable protic solvents are, for example, a $C_1$-$C_6$ alkanol or water or an aqueous $C_1$-$C_6$ alkanol or other solvent systems which contain water, such as aqueous dimethylformamide, aqeous hexamethylphosphoramide, aqueous tetrahydrofuran or aqueous ethylene glycol dimethyl ether.

The process is usually carried out in a pH range from 1 to 11, and preferably at pH 4 to 8.

Another process according to the invention for the preparation of the 3"-N-alkylated amino-trisaccharide derivatives consists of alkylation of the tetra-N-protected amino-trisaccharides in question, with a non-blocked 3"-methylamino group, with alkyl halides.

$$R_1\text{—Hal}$$

in which
$R_1$ has the abovementioned meaning and Hal denotes a halogen atom, such as a chlorine, bromine or iodine atom, Such alkylation reactions on amines are already known from the literature (see, for example, Houben-Weyl, Methoden der organischen Chemie (Methods of Organic Chemistry), Volume XI, 1, Georg Thieme Verlag, Stuttgart 1957). These reactions are preferably carried out in the presence of a diluent which is inert under the reaction conditions, and preferably in one in which the reactants are readily soluble. Preferred diluents of this type are ethers, such as tetrahydrofuran, ethylene glycol dimethyl ether or dioxane, ketones, such as acetone or methyl ethyl ketone, alcohols, dimethylacetamide and dimethylformamide. It is particularly preferable to use dimethylformamide as the solvent in these reactions. Depending on the reactivity of the alkyl halide employed, 1 to 10 molar equivalents of alkylating agent are used and the reaction is carried out at pH values from about 5 to about 12. It is preferable to use an auxiliary base here, in order to trap the hydrogen halide liberated during the reaction. Examples of appropriate bases are alkali metal hydroxides, alkaline earth metal hydroxides, alkali metal carbonates and alkaline earth metal carbonates, alkaline earth metal oxides and carbonates and oxides of heavy metals, such as lead carbonate and silver carbonate, as well as mercury oxide or silver oxide. In principle, all compounds which are stable under the reaction conditions and which are capable of trapping the hydrogen halide formed can be used as auxiliary bases.

It may be advantageous for the tetra-N-protected amino-trisaccharides with a tertiary 3"-amino group which are obtained as crude products to be subjected to liquid/liquid extraction, for purification, and then for the product thus purified to be demethylated as described below.

One of the preferred processes for splitting off the 3''-N-methyl group from the crude or extractively purified trisaccharides with a tertiary 3''-amino group which have been obtained as described above is oxidated demethylation with customary oxidising agents.

Examples of oxidising agents are heavy metal salts, peroxides, halogens, halogen oxyacids and salts thereof, nitrogen oxides and molecular oxygen. Preferred oxidising agents are permanganates, manganates, manganese dioxide, chromium trioxide, bichromates, chromates, alkyl-chromates, chromyl chloride, selenium dioxide, cobalt-III salts, cerium-IV salts, potassium hexacyano-ferrate-III, copper oxide, lead oxide, mercury oxide, mixtures of hydrogen peroxide and iron-III salts, iron-II salts, selenium oxide, osmium tetroxide, vanadates, tungstic acid and/or chromic acid, lead tetraacetate, chlorine, bromine, iodine, hypochlorates, chlorites, hypobromates, bromates, periodates, dinitrogen monoxide, nitrogen dioxide and air. If molecular oxygen is used, noble metals, such as platinum, palladium, rhodium, ruthenium or rhenium, and nickel are preferably used as catalysts.

Particularly preferred oxidising agents are manganese dioxide, potassium hexacyanoferrate-III and potassium permanganate.

The splitting reaction is preferably carried out in the presence of a diluent which is inert under the reaction conditions, preferably one in which the reactants dissolve. Suitable diluents of the type mentioned are water or mixtures of water and methanol, ethanol, i-propanol, tetrahydrofuran, dimethylformamide, dioxane, pyridine, ethylene glycol dimethyl ether and acetone.

The reaction is generally carried out at a pH value of 3 to 12, depending on the nature of the oxidising agent used. The pH value can be established by adding an appropriate acid or base. Those acids or bases which do not decompose the starting compounds or the end product and cause no decrease in the activity of the oxidising agents are to be used. Rather, it is desirable for them to increase the activity of the oxidising agents. Inorganic acids which can be used are, for example, hydrochloric acid or sulphuric acid, and organic acids which can be used are, for example, acetic acid or formic acid. Examples of appropriate bases are ammonium hydroxide, alkali metal hydroxides, alkaline earth metal hydroxides, alkali metal alcoholates and alkali metal and alkaline earth metal salts of carboxylic acids.

The pH value can be established either before the start of the reaction or during the reaction.

The reaction is generally carried out at temperatures of $-30°$ C. to $100°$ C., preferably of $-20°$ to $0°$ C. The reaction time is half an hour to 50 hours. In general, the reaction is carried out under normal pressure.

The splitting off of the 3''-N-methyl-groups is also achieved by reaction with chloroformic acid esters in the presence of auxiliary bases, the methyl group being replaced by the corresponding alkyl- or aryl-oxycarbonyl group and penta-N-blocked compounds being formed.

In the last part of the process according to the invention, the protective groups are split off from the amino groups in the customary manner.

The sulphenyl groups can be split off either with nucleophiles, such as hydrogen sulphide, thiophenol or 2-mercaptobenzthiazole, if appropriate also in the presence of mineral acids, or by heating with inorganic bases, such as alkali metal hydroxides or alkaline earth metal hydroxides, if necessary under increased pressure.

Acyl protective groups, such as acetyl, ethoxycarbonyl or t-butoxycarbonyl, can be split off with aqueous alkali metal hydroxide or alkaline earth metal hydroxide or with acids, such as trifluoroacetic acid or boron trifluoride etherate, in organic solvents or mixtures of organic solvents in water.

The end products obtained after splitting off the protective groups are isolated as free bases or in the form of pharmaceutically usable acid addition salts.

Compared with the processes known hitherto, the process according to the invention represents a substantial improvement. The process according to the invention is broadly applicable and gives products in high yields with relatively little technological effort.

The purity of the intermediate products and end products obtained was determined densitometrically via Craig distribution, or by high pressure liquid chromatograhy (HPLC). The following solvent systems were used in the thin layer chromatography in the examples:

Mobile phase mixture G:

1000 ml of methanol, 1000 ml of methylene chloride and 1000 ml of 15% strength ammonium hydroxide are shaken thoroughly for 5 minutes. After separating off the lower phase, 1% of methanol (=10 ml) is added to this phase and the mixture is used for the chromatography.

Mobile phase mixture E:

A mixture of 200 ml of methylene chloride, 400 ml of methanol and 100 ml of 20% strength ammonium hydroxide.

The crude products used in the following Examples can be obtained by a method wherein the corresponding fermentation medium is acidified and then filtered; calcium ions are then removed, if necessary, with oxalic acid. The solution is neutralised with aqueous ammonium hydroxide and treated with a cation exchanger resin ($NH_4^\oplus$ form), onto which the aminoglycosides are bonded; the exchanger is wased, and eluted with aqueous ammonium hydroxide. The crude solutions of aminotrisaccharide which are thus obtained are evaporated until the ammonia has been removed. The following Examples, 3,4,6 and 8 to 16 illustrate the process of the present invention, whereas the remaining Examples illustrate the pre-purification of the crude product, the removal of protective groups or the formation of chemical derivatives.

EXAMPLE 1

Penta-N-(o-nitrophenylsulphenyl)-sisomicin-crude product 285 g of o-nitrophenylsulphenyl chloride in 686 ml of tetrahydrofuran, and 186 ml of 8 N sodium hydroxide solution were simultaneously added dropwise to 442 g of 50% strength crude sisomicin in 400 ml of water and 800 ml of tetrahydrofuran at pH 12 to 14 in the course of 30 minutes, whilst stirring. The temperature thereby rose to about 45° C. The stirrer was switched off, the aqueous phase was separated off and the organic phase was evaporated in vacuo in a rotary evaporator. The residue was dried in vacuo. Yield of crude product: 670 g. In the thin layer chromatogram (mobile phase system methylene chloride/methanol=85/5), the title compound was to be found as the main product. Rf=0.87.

EXAMPLE 2

1,2',3,6'-Tetra-N-(o-nitrophenylsulphenyl)-sisomicin 130 g of o-nitrophenylsulphenic acid p-nitro-phenyl ester were added to 90 g of 50% strength crude sisomicin in 100 ml of methanol and 900 ml of methylene chloride, and, after about one hour, the reaction mixture was poured onto 3000 ml of methanol, the precipitate was digested with 500 ml of methylene chloride and, after filtration, the residue was dried. Yield of crude product: 101 g. In the thin layer chromatogram (mobile phase system: methylene chloride/methanol=9/1), the title compound was to be found as the main product. Rf=0.14.

EXAMPLE 3

Pure sisomicin from crude sisomicin via 1,2',3,6'-tetra-N-acetyl-3"-N-(n-butoxycarbonyl)-sisomicin 3.1 1,2',3,6'-Tetra-N-acetylsisomicin (crude product)

1020 ml of aqueous crude sisomicin solution with a sisomicin content of 122 g were diluted with 400 ml of water, and after cooling to about 5° C., 240 ml of acetic anhydride were slowly added. The mixture was then evaporated in vacuo and the acetic acid was thereby largely distilled off. Residual acetate was removed by treatment with an anion exchanger resin ("Lewatit" MP 500, OH$^\ominus$ form) in aqueous solution. After separating off the resin, the mixture was evaporated to a syrup in vacuo. The crude product thus obtained contained 1,2',3,6'-tetra-N-acetylsisomicin as the main product (Rf=0.21; mobile phase system G).

3.2 1,2',3,6'-Tetra-N-acetyl-3"-N-(n-butoxycarbonyl)sisomicin (crude product)

The crude product obtained in 3.1 was dissolved in 840 ml of ethanol and 160 ml of water, and 185 g of sodium carbonate were then added. A solution of 185 ml of n-butyl chloroformate in 185 ml of acetone was added dropwise at 50° C., 1500 ml of ethanol were then added, the mixture was allowed to cool and the inorganic salts are filtered off. The filtrate was evaporated to a syrup in vacuo and the title compound was obtained as a crude product in the form of a brown-coloured syrup.

3.3 Extractive purification and slitting off of the protective groups, and isolation of pure sisomicin The syrup obtained in 3.2 was dissolved in 750 ml of concentrated aqueous ammonia. Lipophilic impurities were extracted from this solution with two 350 ml portions of methylene chloride. The sisomicin derivative was then isolated by extracting the ammonia solution twenty times with in each case 1500 ml of the lower phase of the system methylene chloride (7 parts by volume), propan-2-ol (0.8 part by volume) and concentrated aqueous ammonia (1.0 part by volume). After evaporating off the extraction agent, 1,2',3,6'-tetra-N-acetyl-3"-N-(n-butoxy-carbonyl)sisomicin was obtained as a colourless residue, which, for further purification, was again subjected to the extraction described above.

In order to split off the protective groups, the pure product was heated under reflux with 880 g of Ba-(OH)$_2$×8H$_2$O in 1500 ml of water. After about 8 hours, the barium salts were separated off by precipitation with CO$_2$ and filtration. The filtrate was deionised with a basic ion exchanger resin ("Lewatit" MP 500, OH$^\ominus$ form). The sisomicin base was removed from the solution by adsorption onto a cation exchanger resin ("Lewatit" CNP-LF, NH$_4^\oplus$ form). The resin adduct thus obtained was washed with water. The sisomicin base was then eluted with 5% strength aqueous ammonia. The eluate was evaporated in vacuo and the residue (sisomicin base) was converted into the sulphate by treatment with sulphuric acid in water. After freeze-drying the product, sisomicin sulphate was obtained as a colourless solid.

Yield: 151 g=80% of theory;
$[\alpha]_D^{20}$ = +105° (c=1.0 in H$_2$O);
purity: 96%.

EXAMPLE 4

Pure sisomicin from crude sisomicin via 1,2',3,6'-tetra-N-acetyl-3"-N-(n-octyloxycarbonyl)-sisomicin 4.1 1,2',3,6'-Tetra-N-acetyl-3"-N-(n-octyloxycarbonyl)sisomicin, crude product 12 ml of acetic anhydride were added dropwise to 12.8 g of crude sisomicin (content of sisomicin: about 55%) in 70 ml of water, whilst stirring. The mixture was evaporated in vacuo and the residue was dissolved in 150 ml of water. The mixture was then deionised by stirring with 150 ml of an anion exchanger resin ("Lewatit" MP 500, OH$^\ominus$ form), the resin was filtered off and the filtrate was evaporated to a syrup in vacuo. This syrup was dissolved in 50 ml of propan-1-ol, 11 g of sodium carbonate were added, and 11 ml of n-octyl chloroformate was added dropwise, whilst stirring. The mixture was stirred for a further four hours at room temperature and 200 ml of methanol and 1.5 g of wood charcoal were then added. The precipitates were removed by filtration and the filtrate was evaporated to a volume of about 100 ml in vacuo. 100 ml of methylene chloride were then added, the precipitate was filtered off and the filtrate was evaporated to a syrup in vacuo. The title compound was thus obtained as a brown crude product.

4.2 Extractive purification and splitting off of the protective groups, and isolation of pure sisomicin The syrup was dissolved in 50 ml of the lower phase of the two-phase system n-butanol/ammonia (concentrated)/n-hexane (ratio of 4.8:5.0:0.2—in each case parts by volume) and the solution was thoroughly stirred with 50 ml of the upper phase of the same system. The upper phase was evaporated in vacuo and the syrup thus obtained was heated under reflux with 40 g of barium hydroxide hydrate in 70 ml of water for 7 hours. The mixture was then adjusted to pH 5, whilst hot, with 20% strength H$_2$SO$_4$, the barium sulphate was centrifuged off, the centrifugate was adjusted to pH 10 to 11 by stirring with an anion exchanger resin ("Lewatit" MP500, OH$^\ominus$ form), the resin was filtered off and the filtrate (about 400 ml) was introduced onto a cation exchanger column (2.5×20 cm "Lewatit" CNP-LF, NH$_4^\oplus$ form, 100 ml). The column was rinsed with 1.3 liters of water and the sisomicin was then eluted with 200 ml of 5% strength aqueous ammonia. After freeze-drying the product, 6.0 g=85% of a colourless solid with a purity of about 95% were isolated.

$[\alpha]_D^{22}$ = +188° (c=1.0 in H$_2$O).

EXAMPLE 5

Penta-N-methoxycarbonylsisomicin, crude product 3.5 g of dimethyl pyrocarbonate were added to 9 g of 50% strength crude sisomicin in 100 ml of methanol, whilst cooling with ice. After half an hour, the mixture was freed from the solvent in vacuo and the residue was dried.

Yield: 13.8 g of crude product;
(Rf of the title compound, as the main product: 0.33, mobile phase system: chloroform with 10% by volume of methanol).

EXAMPLE 6

6.1 Pure sisomicin from crude sisomicin via 1,2',3,6'-tetra-N-methoxycarbonylsisomicin 170 ml of crude sisomicin solution with a sisomicin content of 20.3 g of sisomicin were diluted with 375 ml of water and 100 ml of methanol, and a solution of 28 ml of dimethyl pyrocarbonate in 60 ml of methanol was added at an internal temperature of −8° to −10° C. in the course of one hour, whilst stirring. When the reaction was complete (monitoring by TLC in mobile phase system G), the mixture was evaporated in vacuo and the residue was dried until an amorphous solid was obtained. The title compound, as the main component, had a Rf value of 0.48 (mobile phase system G).

6.2 Extractive purification and isolation of 1,2',3,6'-tetra-N-methoxycarbonylsisomicin The residue from Example 6.1 was dissolved in 340 ml of concentrated aqueous ammonia. This solution was extracted 20 times with in each case 450 ml of a mixture of 340 ml of methylene chloride, which had been saturated with concentrated aqueous ammonia, and 135 ml of n-hexane, the tetra-N-methoxycarbonylsisomicin passing into the organic phase. The combined extract phases were freed from solvent in vacuo, the residue thus obtained was dissolved in 200 ml of concentrated aqueous ammonia and the solution was extracted 20 times with in each case 265 ml of a mixture of one part by volume of n-hexane and 2.5 parts by volume of methylene chloride, which had been saturated with concentrated aqueous ammonia. The combined extracts were freed from solvent in vacuo and the residue was dried until an amorphous solid was obtained.

Yield: 28.0 g;
Rf=0.48 (mobile phase system G);
$[\alpha]_D^{20} = +153°$ (c=1.0 in methanol).

6.3 Splitting off of the protective groups and isolation of pure sisomicin sulphate 28 g of 1,2',3,6'-tetra-N-methoxycarbonyl-sisomicin from Example 6.2 are taken up in 560 ml of water. 84 g of barium hydroxide octahydrate were added and the mixture was then heated to 190° C. in a pressure reaction vessel under a pressure of 20 bars and under a nitrogen atmosphere for about 20 minutes. After cooling the barium salts were precipitated by adding solid carbon dioxide; the salts which had precipitated were filtered off, the residue was washed thoroughly with water and the filtrates were deionised by stirring with 400 ml of basic ion exchanger resin ("Lewatit" MP 500, OH⊖ form). After separating off the resin, the resulting aqueous solution of the sisomicin base was introduced onto a column containing 370 ml of cation exchanger resin ("Lewatit" CNP, NH4+ form), the sisomicin being bonded to the resin. The column was washed with 1000 ml of water and the sisomicin was then eluted with 5% strength aqueous ammonium hydroxide. After evaporating off the ammonia, sisomicin remained as a colourless solid. This was dissolved in 140 ml of water and the alkaline solution was adjusted to pH 4.8 with dilute sulphuric acid. The solution was stirred with active charcoal and filtered, and the filtrate was lyophilised.

Yield of sisomicin sulphate: 27.3 g.
$[\alpha]_D^{20} = +106°$ (c=1.0 in H$_2$O).

EXAMPLE 7

Deblocking of 1,2',3,6'-tetra-N-methoxycarbonyl-sisomicin to give sisomicin 20 g of 1,2',3,6'-tetra-N-methoxycarbonyl-sisomicin in 180 ml of dimethyl sulphoxide and 60 ml of water were stirred with 40 g of potassium hydroxide at 35° C. for 50 hours. According to TLC (Mobile phase system E), the reaction was complete at this point in time.

333 ml of H$_2$O and 77 ml of concentrated ammonia were added and this solution was introduced onto a column containing 230 ml of a cation exchanger ("Lewatit" CNP, NH$_4$⊕ form). The column was eluted with 200 ml of 3% strength ammonia and the eluate was combined with the solution which flowed out and was obtained before the elution. The ammonia was evaporated off in vacuo and the solution which remained was diluted with 500 ml of water and introduced onto a column containing 170 ml of a cation exchanger ("Lewatit" CNP, NH$_4$⊕ form). The exchanger was washed thoroughly with water. It was eluted with 5% strength ammonia and the fractions containing sisomicin were combined and evaporated to dryness in vacuo.

The residue was taken up in water and the mixture is lyophilised. The sisomicin base was thus obtained as a colourless solid. $[\alpha]_D^{22} = +189°$ (c=1.0 in H$_2$O).

EXAMPLE 8

1,2',3,6'-Tetra-N-ethoxycarbonyl-sisomicin from crude sisomicin 100 ml of crude sisomicin solution with a sisomicin content of 22 g were diluted with 700 ml of water and 500 ml of ethanol. 39 ml of diethyl pyrocarbonate in 78 ml of methanol were slowly added dropwise at −10° C. When the reaction was quantitative (monitoring by TLC; mobile phase system G), the solvent was evaporated off in vacuo. The residue was dissolved in 300 ml of concentrated ammonium hydroxide and this solution was extracted by shaking 8 times with in each case 660 ml of an extraction agent consisting of 10 parts by volume of ethyl acetate and 1 part by volume of n-hexane (the mixture was saturated with concentrated ammonium hydroxide). The combined extracts were evaporated in vacuo and dried.

Yield 35 g.
$^{13}$C-NMR (CD$_3$OD/CDCl$_3$): δ=50.86 (C-1), 49.91 (C-2); 46.33 (C-2'); 42.87 (C-6'); and 157.94, 157.73, 157.29 and 157.22 (>C—O) ppm.

The product thus obtained could be deblocked as described in Examples 6.3 or 7.

EXAMPLE 9

Purification of crude gentamicin 55 ml of acetic anhydride were added to 350 ml of a crude gentamicin C solution with a gentamicin C content of about 32 g (proportions of the gentamicin C components, in % by weight: gentamicin C$_{1a}$=25%, gentamicin C$_1$=34% and gentamicin C$_2$=41%). When the addition had ended, the mixture was freed from solvent in vacuo, toluene was added to the residue and the mixture was again evaporated in vacuo. The crude mixture thus obtained was dissolved in 75 ml of water. The solution was deionised by stirring with an anion exchanger resin ("Lewatit" MP 500, OH⊖ form). The solution obtained after separating off the exchanger resin was evaporated in vacuo. The residue was dissolved in 160 ml of ethanol and 30 ml of water, 45 g of sodium carbonate were added, and a solution of 45 ml of n-butyl chloroformate in 45 ml of acetone was added dropwise at 50° C. in the course of about 1.5 hours, whilst stirring. The mixture was allowed to cool, 200 ml of toluene were added and the solvents were distilled off in vacuo. The residue was taken up in 300 ml of ethanol and the mixture was stirred thoroughly. The undissolved material was filtered off and rinsed with ethanol and the combined filtrates were evaporated in vacuo. A crude mixture which contained, as main components, 1,2′,3,6′-tetra-N-acetyl-3″-N-(n-butoxycarbonyl)-gentamicin $C_{1a}$, 1,2′,3,6′-tetra-N-acetyl-3″-N-(n-butoxycarbonyl)-gentamicin $C_2$ and 1,2′,3-tri-N-acetyl-3″,6′-di-N-(n-butoxycarbonyl)-gentamicin $C_1$ was thus obtained. To separate off the impurities, the residue was dissolved in 500 ml of concentrated ammonium hydroxide. This solution was extracted with 150 ml-portions of the lower phase of a system of 7 parts by volume of methylene chloride, 1 part by volume of propan-2-ol and 1 part by volume of concentrated ammonium hydroxide. The gentamicin C derivatives were thus transferred to the extraction agent, and the concomitant products remained in the ammonium hydroxide phase. For further purification, the combined extract phases were evaporated in vacuo and the residue thereby obtained was again subjected to extraction, as described above. The syrup obtained after evaporating the extract phase consisted of a mixture of 1,2′,3,6′-tetra-N-acetyl-3″-N-(n-butoxycarbonyl)-gentamicin $C_{1a}$, 1,2′,3,6′-tetra-N-acetyl-3″-N-(n-butoxycarbonyl)-gentamicin $C_2$ and 1,2′,3-tri-N-acetyl-3″,6′-di-N-(n-butoxycarbonyl)-gentamicin $C_1$. In order to split off the protective groups, 30 g of this compound were dissolved in 150 ml of hot water and, after adding 80 g of barium hydroxide octahydrate, the mixture was heated under reflux for 8 hours (heating bath temperature of about 150° C.). After cooling, the barium salts were precipitated by adding solid carbon dioxide and the precipitate was filtered off. The filtrate was deionised with a basic ion exchanger resin ("Lewatit" MP 500, $OH^{\ominus}$ form). The gentamicin C base was removed from the solution by bonding to a cation exchanger resin ("Lewatit", CNP-LF, $NH_4^{\oplus}$ form). The resin adduct thus obtained was washed with water. The gentamicin C base was then eluted with 5% strength aqueous ammonium hydroxide. The eluate was evaporated in vacuo and the residue was freeze dried.

Gentamicin-C base was thus obtained as a colourless solid, which was converted into the sulphate salt by treating the aqueous solution with sulphuric acid and then lyophilising the mixture.

$[\alpha]_D^{20} = +101°$ (c = 1.06 in $H_2O$) as the sulphate salt.

EXAMPLE 10

Separation of gentamicin $C_1$ form the gentamicin C complex 11 ml of acetic anhydride were added to 70 ml of a crude gentamicin C solution with a gentamicin C content of about 6.5 g (proportions of the gentamicin C components, in % by weight: gentamicin $C_{1a}$=25%, gentamicin $C_1$=34% and gentamicin $C_2$=41%). When the addition had ended, the mixture was freed from solvent in vacuo, toluene was added to the residue and the mixture was again evaporated in vacuo. The crude mixture thus obtained was dissolved in 75 ml of water and this solution was deionised by stirring with an anion exchanger resin ("Lewatit", MP 500, $OH^{\ominus}$ form).

The solution obtained after separating off the exchanger resin was evaporated in vacuo. The residue was dissolved in 42 ml of ethanol and 8 ml of water, 9.25 g of sodium carbonate were added and a solution of 9.3 ml of n-butyl chloroformate in 9 ml of acetone was added dropwise at 50° C. in the course of about 0.5 hour, whilst stirring. The mixture is allowed to cool, 100 ml of toluene were added and the solvents were evaporated off in vacuo. The residue was taken up in 100 ml of methanol and stirred thoroughly. The undissolved material was then filtered off and rinsed with ethanol and the combined filtrates were evaporated in vacuo. A crude mixture which contained, as the main components, 1,2′,3,6′-tetra-N-acetyl-3″-N-(n-butoxycarbonyl)-gentamicin $C_{1a}$, 1,2′,3,6′-tetra-N-acetyl-3″-N-(n-butoxycarbonyl)-gentamicin $C_2$ and 1,2′,3-tri-N-acetyl-3″, 6′-di-N-(n-butoxycarbonyl)-gentamicin $C_1$, was thus obtained.

In order to separate off the gentamicin $C_1$ derivative, the residue was dissolved in 100 ml of concentrated ammonium hydroxide. This solution was extracted with 150 ml of the lower phase of a system of 7 parts by volume of methylene chloride, 0.4 part by volume of propan-2-ol and 1 part by volume of concentrated ammonium hydroxide. The gentamicin $C_1$ derivative was thus transferred into the extraction agent, and the $C_{1a}$ and $C_2$ derivatives remained in the ammonium hydroxide phase. For further purification, the methylene chloride phase was extracted by shaking twice more with in each case 100 ml of concentrated ammonium hydroxide. It was then evaporated in vacuo and dried to constant weight. Pure 1,2′,3-tri-N-acetyl-3″-6′-di-N-(n-butoxycarbonyl)-gentamicin $C_1$ was thus obtained as a colourless solid. $^{13}$C-NMR ($CD_3OD$) rotamer mixture from two rotamers: δ=160.342, 159.909, 158.917 and 158.545 (urethane C=O); 101.672 and 101.241 (C-1′); 99.816 and 98.384 (C-1″); 172-174 (acetyl C=O); 14.025 (urethane —$CH_3$); and 20 (acetyl —$CH_3$) ppm.

In order to split off the protective groups, 3 g of this compound were dissolved in 15 ml of hot water and, after adding 8 g of barium hydroxide octahydrate, the mixture was heated under reflux for 8 hours (heating bath temperature of about 150° C.). After cooling, the barium salts were precipitated by adding solid carbon dioxide and the precipitate was filtered off. The filtrate was deionised with a basic ion exchanger resin ("Lewatit", MP 500, $OH^{\ominus}$ form). The gentamicin $C_1$ base was removed from the solution by bonding to a cation exchanger resin ("Lewatit", CNP-LF, $NH_4^{\oplus}$ form). The resin adduct thus obtained was washed with water. The gentamicin $C_1$ base was then eluted with 5% strength aqueous ammonium hydroxide. The eluate was evaporated in vacuo and the residue was freeze-dried.

Gentamicin $C_1$ base was thus obtained as a colourless solid.

EXAMPLE 11

Preparation of 3″-N-demethyl-3″-N-ethylsisomicin from crude sisomicin

11(a) 1,2′,3,6′-Tetra-N-acetyl-3″-N-ethyl-sisomicin (crude product)

1.04 liters of crude sisomicin solution with a sisomicin content of about 120 g were cooled to about 5° C. 210 ml of acetic anhydride were added dropwise to this solution at this temperature in the course of 45 minutes, whilst stirring well and cooling (acetone/dry ice, very highly exothermic reaction at the start).

The mixture was adjusted to pH 4.5 with 50% strength sodium hydroxide solution and was then allowed to come to room temperature and was diluted with 430 ml of ethanol. 82 ml of acetaldehyde were added to this solution at 0° and the mixture was stirred at room temperature for about 30 minutes.

A solution of 17 g of sodium boranate in 45 ml of 10% strength sodium hydroxide solution and 920 ml of propan-2-ol and 104 ml of water were then added dropwise thereto in the course of 180 minutes, whilst stirring well. After subsequently stirring the mixture for 30 minutes, the reaction was quantitative, according to TLC (mobile phase system G). After neutralising with NaOH, the mixture was evaporated in vacuo to about 600 ml. The concentrate thus obtained contained, as the main product, 1,2',3,6'-tetra-N-acetyl-3"-N-ethylsisomicin. Rf=0.50; mobile phase system G.

(11b) 1,2',3,6'-Tetra-N-acetyl-3"-N-ethylsisomicin-pure product obtained by extraction The ethyl compound was isolated, by extraction, from the concentrate obtained according to Example (11a). 1.4 liters of concentrated ammonium hydroxide were added to the concentrate and the mixture was initially extracted, in a 6 liter separating funnel by stirring with a blade stirrer (750 revolutions/minute), three times with in each case 180 ml of the lower phase of a mixture of methylene chloride/propane-1-ol/NH$_4$OH, in a ratio of 7:0.5:1 (in each case parts by weight), the lipophilic impurities being separated off. The lower phases were in each case discarded; the aqueous phase contained the title compound. For extraction of the desired product from this aqueous phase, the aqueous phase was extracted by stirring 15 times with in each case 700 ml of the lower phase of the mixture of methylene chloride/propan-1-ol/NH$_4$OH—in a ratio of 7:1.5:1 (parts by volume)—by following the procedure described above.

A total of about 160 g of the title compound=92%, relative to sisomicin employed, were thus obtained and were then in the lower phases. Purity: about 95%.

$[\alpha]_D^{22} = +168°$ (c=1.0 CH$_3$OH)

(11c) Oxidative dealkylation to give 1,3,2',6'-tetra-N-acetyl-3"-N-demethyl-3"-N-ethylsisomicin and 1,3,2',6'-tetra-N-acetylsisomicin 17 g of the 3"-N-ethyl compound prepared as described in (11b) were dissolved in 255 ml of water. 11 g of sodium hydroxide were added, whilst cooling with ice. 85 ml of ethanol were then added and the mixture was cooled to about −20° C. 30 g of potassium hexacyanoferrate-III were then added thereto in 10 portions at this temperature in the course of 60 minutes, whilst stirring. After adding the last portion, the mixture was subsequently stirred for a further 30 minutes—according to TLC (mobile phase system G), the reaction was then quantitative.

For working up, the mixture was adjusted to pH 7 with 30% strength sulphuric acid, whilst stirring and cooling, and a solution of 30 g of copper sulphate in 55 ml of water was then added in order to precipitate copper hexacyanoferrate. The mixture was allowed to come to room temperature, whilst stirring, the precipitates were removed by centrifugation and were washed out 4 times with water, the combined centrifugates were adjusted to pH 7 with 50% strength sodium hydroxide solution and the mixture was evaporated into a thin syrup in vacuo (temperature: about 50° to 60° C.). The syrup was taken up in 40 ml of methanol, and 80 ml of acetone and 40 ml of ethyl acetate were successively added, whilst stirring thoroughly. The inorganic salts which had thereby precipitated were filtered off, the residue was washed out thoroughly with acetone/methanol/ethyl acetate (ratio=2:1:1) and the combined filtrates were freed from copper by stirring for a short time with 40 ml of the ion exchanger resin Lewatit SC 108 (H$^\oplus$ form), which had been washed until neutral. The solution thereby became increasingly more acid, and at pH 3 the resin was filtered off and rinsed with methanol and the filtrate was neutralised as rapidly as possible with solid sodium carbonate. The solution thus obtained was evaporated to dryness in vacuo (monitoring by TLC in system G). A product mixture consisting of 1,2',3,6'-tetra-N-acetyl-3"-N-demethyl-3"-N-ethylsisomicin as the main component and 1,2',3,6'-tetra-N-acetyl-sisomicin as a by-product, was thus obtained.

(11d) Separating off the 3"-N-demethyl-3"-N-ethyl compound as the 3"-N-(n-octyloxycarbonyl) derivative For selective N-carbomethoxylation of 1,2',3,6'-tetra-N-acetylsisomicin, 10 g of the oxidation mixture prepared as above were dissolved in 50 ml of methanol and 50 ml of acetone.

The solution was adjusted to pH 11 with saturated methanolic sodium hydroxide solution. 0.2 ml of methyl chloroformate in 0.4 ml of acetone were then added dropwise in the course of 5 minutes, whilst stirring thoroughly, the mixture was subsequently stirred for a further 30 minutes and adjusted to pH 11 as above, and the addition of the chloroformate and the regulation of the pH were repeated a further three times in the manner described. 1,2',3,6'-Tetra-N-acetyl-sisomicin was converted completely into 1,2',3,6'-tetra-N-acetyl-3"-N-methoxycarbonyl-sisomicin, whereas, because of the comparatively lower reactivity of the 3"-ethylamino group, the 3"-N-demethyl-3"-N-ethyl compound had not reacted. All the amino groups in the 1,2',3,6'-tetra-N-acetyl-3"-N-methoxycarbonyl-sisomicin had been blocked, and 1,2',3,6'-tetra-N-acetyl-3"-N-demethyl-3"-N-ethyl-sisomicin still contained an acylatable 3"-ethylamino group, which, in order to lipophilise this derivative, was then urethanised by reaction with n-octyl chloroformate.

For this urethanisation, the solution obtained above was allowed to come to room temperature. 10 g of sodium carbonate were then added, and 5 ml of n-octyl chloroformate were added, whilst stirring thoroughly. After about 60 minutes, a further 5 ml of chloroformate were added, and after a further hour the mixture was worked up (excess chloroformate was trapped with NH$_4$OH).

In order to precipitate the inorganic salts, 150 ml of acetone were added, whilst stirring, and the precipitate was filtered off over a frit. It was rinsed with methanol/acetone=¼ and the combined filtrates were evaporated to a syrup in vacuo at about 50° to 60° C. (TLC in system G).

The syrup thus obtained consisted of 1,2',3,6'-tetra-N-acetyl-3"-N-demethyl-3"-N-ethyl-3"-N-(n-octyloxycarbonyl)-sisomicin, as the main product, and contained 1,2',3,6'-tetra-N-acetyl-3"-N-methoxycarbonylsisomicin, as a by-product. The 3"-N-demethyl derivative, which had been highly lipophilised in the manner described above, was then separated off in a pure form by extraction. For this, the syrup was taken up in 80 ml of water and the 3"-N-(n-octyloxycarbonyl)-derivative was extracted quantitatively into the upper phase by stirring with 40 ml of n-butanol and 48 ml of n-hexane (about 10 minutes). The derivative was separated off and extracted by stirring twice with in each case 20 ml of water. The upper phase was evaporated to a syrup in vacuo. The combined lower phases, which contained the 3″-N-methoxycarbonylsisomicin, were worked up to give sisomicin.

(11e) 3″-N-Demethyl-3″-N-ethylsisomicin from 1,2′,3,6′-tetra-N-acetyl-3″-N-demethyl-3″-N-ethyl-3″-N-(n-octyloxycarbonyl)-sisomicin The syrup resulting from evaporating the upper phase obtained as described in Example (11d) was taken up in 40 ml of water and, after adding 24 g of barium hydroxide 8H$_2$O, the mixture was heated for 5 to 6 hours (bath temperature: 150° C.). The octanol liberated was thereby distilled off (monitoring of the reaction by TLC in system E). The mixture was allowed to cool to about 100° C., the barium ions were precipitated by adding 30% strength sulphuric acid (dropwise) until the pH was 5 and the mixture was allowed to come to room temperature. The barium sulphate was removed by centrifugation, the centrifugate was extracted by shaking with 50 ml of methylene chloride or ethyl acetate and the aqueous phase was stirred with 1 g of active charcoal. The charcoal was filtered off and the filtrate was stirred with about 120 ml of the ion exchanger resin "Lewatit" MP 500, OH$^\ominus$ form, until the pH was 11, by which means 3″-N-demethyl-3″-N-ethylsisomicin was converted into the free base. The ion exchanger was filtered off and rinsed with water. The combined filtrates were absorbed onto a cation exchanger resin ("Lewatit" CNP-LF, NH$_4^\oplus$ form) in a column. (Column dimensions: 1×20 cm, flow rate: about 3 drops/second). The resin was washed with 1 to 1.5 liters of water. The product was then eluted with 50% strength NH$_4$OH (flow rate: about 3 drops/second). The fractions which contained 3″-N-demethyl-3″-N-ethylsisomicin were combined (a total of about 70 ml) and were evaporated to dryness in vacuo. The product was obtained as a colourless solid by taking up the residue in methanol/methylene chloride and evaporating the mixture again. $^{13}$C-NMR (D$_2$O): δ=68.20 (C-2″); 63.08 (C-3″); 51.35 (C-1); 49.58 (C-3); 45.85 (C-6′); 41.65 (—CH$_2$—CH$_3$); and 11.90 (—CH$_2$—CH$_3$) ppm.

In order to convert the product into the corresponding sulphate, a solution of 3″-N-demethyl-3″-N-ethylsisomicin in water was adjusted to pH 4.8 with dilute sulphuric acid. It was then freeze-dried. $[\alpha]_D^{20} = +107°$ (c=1.0 water).

EXAMPLE 12

1,2′,3,6′-Tetra-N-acetyl-3″-N-ethyl-sisomicin from crude sisomicin 33 liters of crude sisomicin solution with a sisomicin content of about 3 kg were cooled to 0° to 2° C. in a 100 liter enamel stirred kettle, whilst stirring. 6 liters of acetic anhydride were added to this solution in the course of 2 hours, whilst stirring vigorously, the temperature being kept between 5° and 7° C. The mixture was subsequently stirred for 30 minutes and 10% strength sodium hydroxide solution was then added, whilst stirring and cooling, until the pH was 4.2. 12 liters of ethanol were then added and the solution was cooled to 5° C. 2.5 liters of pre-cooled acetaldehyde were added at this temperature, whilst stirring, and a solution of 390 g of sodium borohydride, 1.3 liters of 10% strength sodium hydroxide solution and 26 liters of propan-2-ol in 6 liters of water was added, whilst stirring, whilst passing through nitrogen steadily for 30 minutes. The mixture was subsequently stirred for about a further hour and the reaction solution was concentrated in vacuo to a final volume of 15 liters.

35 liters of concentrated aqueous ammonium hydroxide were added to this solution, and 50 liters of a crude solution containing about 4.3 kg of 1,2′,3,6′-tetra-N-acetyl-3″-N-ethyl-sisomicin as the main product were thus obtained. For the extraction with water, this solution was diluted to a content of 5.2% by weight of 1,2′,3,6′-tetra-N-acetyl-3″-N-ethylsisomicin.

EXAMPLE 13

Purification of 1,2′,3,6′-tetra-N-acetyl-3″-N-ethylsisomicin—crude product, by continuous countercurrent extraction In the first part of the process, lipophilic impurities were separated off. For this, 13.0 liters per hour of an aqueous-ammoniacal solution, prepared according to Example 12, containing 5.2% by weight of 1,2′,3,6′-tetra-N-acetyl-3″-N-ethylsisomicin ($\hat{=}$686 g/hour) were passed in countercurrent with 5.4 liters per hour of an extraction agent consisting of a mixture, saturated with 25% strength aqueous ammonium hydroxide, of 7 parts by volume of methylene chloride and 0.25 parts by volume of propan-2-ol in a ARD extractor with a nominal width of 72 mm. The extraction agent phase, which contained the lipophilic impurities, was evaporated in vacuo in an evaporator unit, and the solvent mixture obtained after condensation was adjusted to the original mixture values in a stock vessel. It was then recycled to the process as the extraction agent.

The raffinate phase, which had been freed from the lipophilic impurities, was passed continuously to a second ARD extractor unit with a nominal width of 150 mm, and was passed in countercurrent with 90 liters per hour of a solvent consisting of a mixture, which had been saturated with concentrated aqueous ammonium hydroxide, of 7 parts by volume of methylene chloride and 2 parts by volume of propan-2-ol.

The aqueous-ammoniacal raffinate phase was taken off at the top end of the column. It had a residual content of 1,2′,3,6′-tetra-N-acetyl-3″-N-ethyl-sisomicin of about 0.1% by weight and contained, above all, the hydrophilic impurities. The extract phase, about 107 kg per hour, removed at the bottom of the column contained 0.615% by weight of 1,2′,3,6′-tetra-N-acetyl-3″-N-ethylsisomicin, corresponding to 658 g of product per hour. The extract phase was concentrated in vacuo. The solvent evaporated off was recovered and employed again in the process. The overall yield in this extraction process was about 97% of 1,2′,3,6′-tetra-N-acetyl-3″-N-ethylsisomicin. The product was 95% pure.

EXAMPLE 14

Mixture of 1,2′,3,6′-tetra-N-acetyl-3″-N-ethyl-3″-N-demethyl-3″-N-isopropoxycarbonyl-sisomicin and 1,2′,3,6′-tetra-N-acetyl-3″-isopropoxycarbonyl-sisomicin 180 g of the 1,2′,3,6′-tetra-N-acetyl-3″-N-ethylsisomicin obtained according to Example 13 were dissolved in 270 ml of methanol and 250 ml of water in a 4 liter three-necked flask with a stirrer, dropping funnel and internal thermometer and a solution of 64 g of sodium hydroxide in 400 ml of water was added, whilst cooling. The mixture was then cooled to an internal temperature of −15° to −17° C., and a solution of 240 g of potassium hexacyanoferrate-III in 600 ml of water was added dropwise at this temperature in the course of 3 hours, whilst further stirring. When the addition had ended, the mixture was subsequently stirred for a further 45 minutes. It was allowed to come to 0° C., 5 g of sodium sulphite were added, the mixture was allowed to come to room temperature and 500 ml of methanol and 240 g of anhydrous sodium carbonate were successively added. The mixture was warmed to 40° C., whilst stirring, and 700 ml of isopropyl chloroformate in 300 ml of acetone were then added in the course of 3 hours. After stirring the solution at 40° C. for 15 hours, it was evaporated in vacuo until the methanol had been removed. The solution thereby obtained was poured into 3 liters of water, and 1.4 liters of concentrated aqueous ammonium hydroxide were then added, whilst stirring. The mixture was filtered and extracted with in each case 5 liters of the lower phase of the system methylene chloride (7 parts by volume), propan-2-ol (2.5 parts by volume) and 25% strength aqueous ammonium hydroxide (2 parts by volume), whereupon the title compounds migrated to the organic phase, which was evaporated to a syrup in vacuo. Salt-like compounds and any polar concomitant products present remained in the ammonia phase.

The syrup obtained by evaporation of the extraction agent consisted of 1,2',3,6'-tetra-N-acetyl-3''-N-demethyl-3''-N-ethyl-3''-N-isopropoxycarbonyl-sisomicin, as the main product (Rf=0.51; mobile phase system G) and 1,2',3,6'-tetra-N-acetyl-3''-N-isopropoxycarbonyl-sisomicin as the secondary component (Rf=0.41; system G).

EXAMPLE 15

1,2',3,6'-Tetra-N-acetyl-3''-N-demethyl-3''-N-ethyl-3''-N-isopropoxycarbonyl-sisomicin The title compound was obtained by extraction from the mixture which contained 1,2',3,6'-tetra-N-acetyl-3''-isopropoxycarbonyl-sisomicin and was prepared as described in Example 14. For this extraction, 200 g of the syrupy product mixture prepared according to Example 14 were dissolved in 1.5 liters of 25% strength aqueous ammonium hydroxide. This solution was extracted 12 times with in each case 3 liters of the lower phase of a mixture of 7 parts by volume of methylene chloride, 0.6 part by volume of propan-2-ol and 1 part by volume of concentrated ammonia. The combined extracts were evaporated in vacuo and the residue was again subjected to the extraction process described above. The extract phase thereby obtained was evaporated in vacuo and the residue was dried to constant weight. The title compound was thus obtained in a pure form as an amorphous solid. $^{13}$C-NMR (CD$_3$OD): 101.257 (C-1''); 50.709 (C-1); 66.563 (C-3''); 173.629, 173.549, 173.452 and 173.971 (acetyl-C=O); 159.909 ((CH$_3$)$_2$CH-O-CO-); and 15.18 (3''-NH-CH$_2$-CH$_3$) ppm.

1,2',3,6'-Tetra-N-acetyl-3''-N-isopropoxycarbonyl-sisomicin was obtained from the combined ammoniacal raffinate phases by evaporation. $^{13}$C-NMR (CD$_3$OD): 101.064 (C-1''); 50.693 (C-1); 66.258 (C-3''); 173.613, 173.452, 172.971 and 172.923 (acetyl-C=O); 159.828 ((CH$_3$)$_2$CH-O-CO-); and 34.662 (N-CH$_3$) ppm.

The protective groups could be split off as described in Example 16. The sisomicin thereby obtained could then be re-used.

EXAMPLE 16

3''-N-Demethyl-3''-N-ethylsisomicin 95 g of the 1,2',3,6'-tetra-N-acetyl-3''-N-demethylethyl-3''-N-isopropoxycarbonyl-sisomicin prepared according to Example 15 were heated under reflux with 300 g of barium hydroxide octahydrate in 500 ml of water. After cooling the mixture, the barium ions were precipitated by adding solid carbon dioxide, the barium carbonate was filtered off, the filtrate was treated with a basic ion exchanger resin ("Lewatit" MP 500, OH$^-$ form) until the pH was 11 and this solution was introduced onto a column charged with a cation exchanger resin ("Lewatit" CNP-LF, NH$_4^\oplus$ form). The resin, onto which the 3''-N-demethyl-3''-N-ethyl-sisomicin was bonded, was washed with water. The title compound was then eluted with 5% strength aqueous ammonium hydroxide and the eluate was evaporated in vacuo until all of the ammonia had been removed. The concentrate was freeze-dried and the title compound was obtained as a colourless solid.

$[\alpha]_D^{20} = +188°$ (c=1.0 H$_2$O)

EXAMPLE 17

1,2',3,6'-Tetra-N-acetyl-3''-N-demethyl-3''-N-ethyl-sisomicin by manganese dioxide oxidation 10 g of 1,2',3,6'-tetra-N-acetyl-3''-N-ethylsisomicin were dissolved in 200 ml of tetrahydrofuran and 25 ml of methanol and the solution was heated with 40 g of manganese dioxide, whilst stirring thoroughly. When the reaction was complete (monitoring by thin layer chromatography in system G), the precipitates were filtered off and washed and the filtrate was evaporated to dryness in vacuo. The residue was dissolved in water and stirred with wood charcoal. The mixture was filtered and the filtrates were evaporated to dryness in vacuo, whereupon the title compound precipitated as an amorphous solid.

Rf=0.35 (system G).

EXAMPLE 18

1,2',3,6'-Tetra-N-acetyl-3''-N-demethyl-3''-N-ethyl-sisomicin by manganese dioxide oxidation in water 1 g of 1,2',3,6'-tetra-N-acetyl-3''-N-ethyl-sisomicin were dissolved in 20 ml of water and the solution was stirred with 8 g of activated manganese dioxide at 0° C. When the reaction was complete (monitoring by TLC in system G), the precipitate was filtered off and washed and the filtrate was evaporated to dryness in vacuo. The residue was dissolved in 5 ml of methanol and 20 ml of methylene chloride, the solution was filtered and the filtrate was evaporated. The title compound was obtained as a colourless solid.

Rf=0.35 (system G).

EXAMPLE 19

1,2',3,6'-Tetra-N-acetyl-3''-N-demethyl-3''-N-ethyl-sisomicin by manganese dioxide oxidation in water/acetic acid 1.2 kg=1.87 moles of 1,2',3,6'-tetra-N-acetyl-3''-N-ethyl-sisomicin were dissolved in 24 liters of water in a 50 liter stirred kettle. The pH was adjusted to 6.5 with 20% strength acetic acid, whilst stirring, and 9.6 kg of activated manganese dioxide were then added. The pH was adjusted to 6.0 with sodium hydroxide solution, and stirring was continued for 15 hours. The batch was then filtered off over filter sheets, the residue on the filter (MnO$_2$) was washed with 24 liters of water and the filtrate was concentrated to a syrup in a thin film evaporator. Yield =86.4% (established by determining the content of the syrup by HPLC).

The protective groups were then split off as described in Example 16.

EXAMPLE 20

20.1 1,2',3,3'',6'-Penta-N-acetyl-sisomicin (crude product)

339 g of an aqueous solution of crude sisomicine with a sisomicin content of 36 g were concentrated in vacuo to 87 g. The solution was then diluted with 108 ml of acetone and 84.5 ml of acetic acid anhydride were added dropwise with stirring at 20° C. After 2.5 hours the reaction mixture was diluted with 72 ml of H$_2$O and adjusted to a pH-value of 6.5 by adding 30% strength sodium hydroxide solution. Then the mixture was evaporated in vacuo to 322 g. 393 g of concentrated aqueous ammonia were added and the mixture was left at room temperature for 18 hours. It contains the title compound as the main product. (Rf=0.24 in mobile phase system G).

20.2 Purification by extraction, removal of protective groups and isolation of pure sisomicin The solution obtained according to 20.1 was extracted 25 times with in each case 322 g of the lower phase of a mixture (being in phase equilibrium) of 7 parts by volume of methylene chloride, 4 parts by volume of propan-2-ol and 4 parts by volume of concentrated aqueous ammonia. The combined extracts were freed from solvents in vacuo, 1,2',3,3'',6'-penta-N-acetyl sisomicin being obtained as a colourless residue.

Splitting off the protective groups and working up was carried out as described in Example 3.3.

Yield of sisomicin sulphate: 80%, Degree of purity: 96.7%.

EXAMPLE 21

21.1 1,2',3,3'',6'-Penta-N-acetyl-gentamicin-C (crude product 100 g of an aqueous solution of crude gentamicin (as in Example 9) with a gentamicin-C-content of 9 g were concentrated in vacuo to 22 g. The solution was then diluted with 27 ml of acetone and 23 ml of acetic acid anhydride were added dropwise with stirring at 20° C. After 2.5 hours the reaction mixture was diluted with 17.2 ml of H$_2$O and adjusted to a pH-value of 6.5 by adding 30% strength sodium hydroxide solution. Then the mixture was evaporated in vacuo to 80 g. 100 g of concentrated aqueous ammonia were added and the mixture was left at room temperature for 18 hours. If contains the title compound as the main product.

21.2 Purification by extraction, removal of protective groups and isolation of pure gentamicin-C The solution obtained according to 21.1 was extracted 25 times with in each case 322 g of the lower phase of a mixture (being in phase equilibrium) of 7 parts by volume of methylene chloride, 3 parts by volume of propan-2-ol and 3 parts by volume of concentrated aqueous ammonia. The combined extracts were freed from solvents in vacuo, 1,2',3,3'',6'-penta-N-acetyl-gentamicin-C being obtained as a colourless residue.

Splitting off the protective groups and working up was carried out as described in Example 9.

$[\alpha]_D^{20} = +102,5°$ (c=2.0 in H$_2$O) for the sulphate.

What is claimed is:

1. A process for the preparation of a pure aminoglycoside antibiotic, which comprises acylating or arylsulphenylating (a) a pre-purified compound of the formula

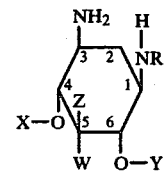

wherein
X denotes a radical of the formulae

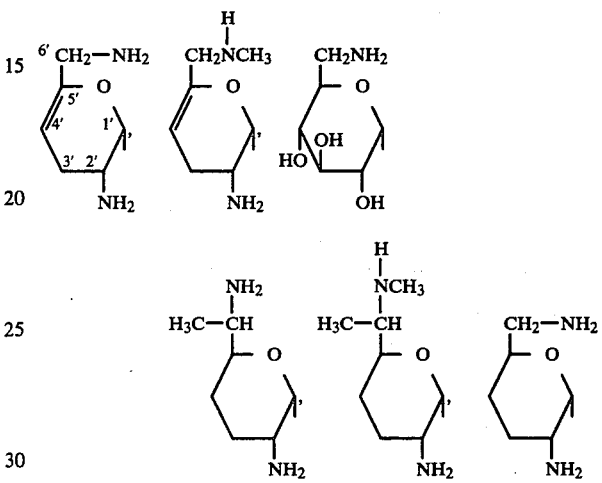

Y denotes a radical of the formulae

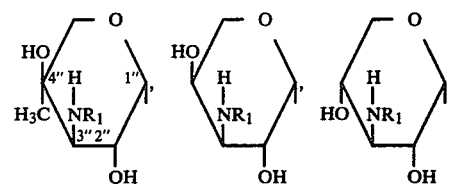

R denotes a hydrogen atom or an ethyl group,
R$_1$ denotes a C$_1$ to C$_6$ alkyl group, and one of the radicals Z or W denotes hydrogen and the other radical Z or W denotes hydrogen or hydroxyl,
to give a compound of the formula

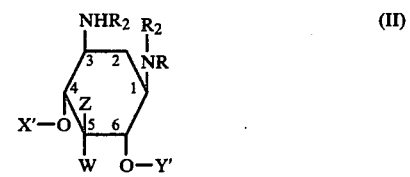

wherein
X' represents a radical of the formulae

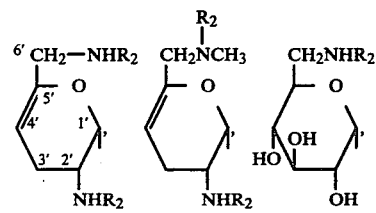

-continued

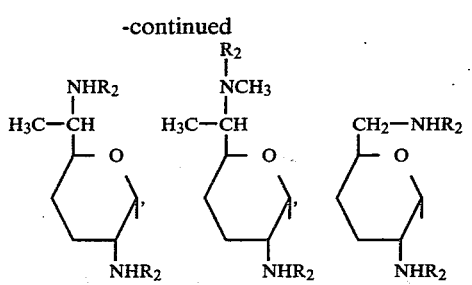

Y' represents a radical of the formulae

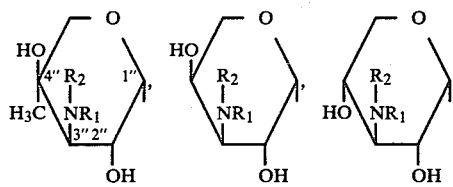

the radicals $R_2$ are identical or different and represent a hydrogen atom or an acyl or arylsulphenyl protective group, with the proviso that at most two of the radicals $R_2$ represent hydrogen atoms, and R, $R_1$, Z and W have the abovementioned meaning, (b) subjecting the compound of the formula (II) from step (a) to liquid/liquid extraction in a two-phase aqueous/organic solvent system and isolating said compound of the Formula (II) from the extracts, and (c) then splitting off the protective group(s).

2. A process according to claim 1, in which one or more of the radicals $R_2$ denote an acyl protective group of the formula

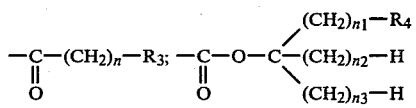

in which $R_3$ and $R_4$ independently of each other denote a hydrogen atom or a phenyl radical optionally monosubstituted or disubstituted by nitro, $C_1$–$C_4$-alkoxy, halogen or phenyl and n, $n_1$, $n_2$ and $n_3$ independently of one another are 0, 1, 2, 3, 4, or 5, or a sulphenyl protective group of the general formula $$-S-R_5-$$

in which $R_5$ denotes a phenyl or di-or tri-phenylmethyl radical optionally monosubstituted or disubstituted by nitro, $C_1$—$C_4$—alkoxy, halogen or phenyl.

3. A process according to any of claim 1 or 2, in which the compound of Formula (I) is sisomicin, 5-episisomicin, netilmicin, gentamicin or 3''-N-demethyl-3''-ethylsisomicin.

4. A process according to claim 3 in which all the groups $R_2$ represent acetyl groups.

5. A process according to claim 1 or 2 in which aqueous ammonium hydroxide is used as the aqueous phase of the two-phase aqueous/organic solvent system in stage (b).

6. A process according to claim 5, in which the two-phase aqueous/organic solvent system is formed when an aqueous ammonium hydroxide solution is brought together with an organic solvent (A) which is immiscible with aqueous ammonium hydroxide or miscible with aqueous ammonium hydroxide only to a limited extent and with a further organic solvent (B), solvent (B) or immiscible with aqueous ammonium hydroxide, the components are then mixed thoroughly until equilibrium is established, and the phases are then allowed to separate from one another and used for the extraction.

7. A process according to claim 6, in which the two-phase aqueous/organic solvent system is obtained from a mixture of n-butanol, ammonium hydroxide and n-hexane; or methylene chloride, ammonium hydroxide and propan-2-ol.

8. A process according to claim 1 or 2, in which the proportion of organic phase to aqueous phase in the two-phase aqueous/organic solvent system is 0.5:1 to 30:1.

9. A process according to claim 8, in which the proportion of organic phase to aqueous phase in the two-phase aqueous/organic solvent system is 5:1 to 20:1.

10. A process according to claim 1 or 2 in which the extraction is carried out at a temperature between 10° and 60°.

11. A process according to any of claim 1 or 2, in which the extraction is carried out as a countercurrent extraction.

12. A process according to claim 1 or 2, in which radical $R_1$ denotes a methyl or ethyl group.

13. A process according to claim 1 or 2, in which in step (a) after the acylation or arysulphenylation, where at least one of the radicals $R_2$ denotes a hydrogen atom, a protective grouping is formed on one or more of the unprotected amino groups.

14. A process according to claim 1 or 2, in which in step (b), where at least one of the radicals $R_2$ denotes a hydrogen atom, a protective grouping is formed on one or more of the unprotected amino groups of the compound isolated from the extracts.

15. A process according to claim 3, in which the preparation is carried out without the formation of protective groups on any unprotected amino groups.

16. A process according to claim 2, wherein (a) crude sisomicin is acetylated on the amino groups in the 1,2',3 and 6'-positions, the product is ethylated on the 3''-amino group by reductive alkylation with acetaldehyde, (b) the product thus obtained is subjected to liquid/liquid extraction in a two-phase aqueous/organic solvent system and 1,2',3,6'-tetra-N-acetyl-3''-N-ethyl-sisomicin is isolated from the extracts, the isolated product is demethylated on the 3''-amino group (c) the protective groups are split off.

* * * * *

UNITED STATES PATENT AND TRADEMARK OFFICE
CERTIFICATE OF CORRECTION

PATENT NO. : 4,380,625
DATED : April 19, 1983
INVENTOR(S) : Peter Stadler et al

It is certified that error appears in the above-identified patent and that said Letters Patent is hereby corrected as shown below:

Col. 5, line 24  Delete "ossible" and insert --Possible--

Col. 7, line 24  Delete "free" and insert --further--

Col. 13, line 45  Delete "slitting" and insert --splitting--

Col. 23, line 34  After "3" insert --N- --

Col. 28, line 14  Before "or immiscible" insert omitted words --being miscible--

Signed and Sealed this

Fifth Day of July 1983

[SEAL]

Attest:

GERALD J. MOSSINGHOFF

Attesting Officer

Commissioner of Patents and Trademarks